US012779064B2

(12) United States Patent
Furukawa et al.

(10) Patent No.: US 12,779,064 B2
(45) Date of Patent: Nov. 3, 2026

(54) STERILIZATION DEVICE, STERILIZATION METHOD, ACTIVE OXYGEN SUPPLY DEVICE, AND DEVICE FOR TREATMENT WITH ACTIVE OXYGEN

(71) Applicant: CANON KABUSHIKI KAISHA, Tokyo (JP)

(72) Inventors: Takumi Furukawa, Shizuoka (JP); Kazuhiro Yamauchi, Shizuoka (JP); Masaki Ozawa, Shizuoka (JP); Kenji Takashima, Kanagawa (JP); Yuichi Kikuchi, Shizuoka (JP); Shota Kaneko, Tokyo (JP); Masatsugu Hongo, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 722 days.

(21) Appl. No.: 18/090,623

(22) Filed: Dec. 29, 2022

(65) Prior Publication Data

US 2023/0139536 A1 May 4, 2023

Related U.S. Application Data

(63) Continuation of application No. PCT/JP2021/024666, filed on Jun. 30, 2021.

(30) Foreign Application Priority Data

Jun. 30, 2020 (JP) ................................ 2020-113518
Oct. 21, 2020 (JP) ................................ 2020-176945
(Continued)

(51) Int. Cl.
*A61L 2/10* (2026.01)
*A61L 2/14* (2006.01)

(52) U.S. Cl.
CPC .. *A61L 2/10* (2013.01); *A61L 2/14* (2013.01)

(58) Field of Classification Search
CPC ..... A61L 2/10; A61L 2/14; A61L 2/20; A61L 2/202; A61L 2101/00; A61L 2202/11; H05H 2245/36; H05H 1/2439; H05H 1/24
See application file for complete search history.

(56) References Cited

U.S. PATENT DOCUMENTS 5,510,158 A 4/1996 Hiramoto et al.
8,168,122 B2 5/2012 Lee
(Continued)

FOREIGN PATENT DOCUMENTS

CN 1997773 A 7/2007
CN 103691246 A * 4/2014
(Continued)

OTHER PUBLICATIONS

May 24, 2024 Office Action in Korean Patent Application Pub. No. 10-2022-7044636.
(Continued)

*Primary Examiner* — Regina M Yoo
(74) *Attorney, Agent, or Firm* — Venable LLP

(57) ABSTRACT

A sterilization device or the like is equipped with a plasma generator and an ultraviolet light source, wherein the plasma generator is a plasma actuator provided with a first electrode and a second electrode with a dielectric in-between, and in which an induced flow including ozone is generated by application of a voltage between the two electrodes, the ultraviolet light source is arranged so as to be able to irradiate the surface of an object to be sterilized, and the plasma actuator is arranged so that the induced flow is supplied to said surface.

5 Claims, 8 Drawing Sheets

(30) Foreign Application Priority Data

Apr. 26, 2021 (JP) ................................ 2021-074162
Jun. 7, 2021 (JP) ................................ 2021-095018

(56) References Cited

U.S. PATENT DOCUMENTS

| | | | |
|---|---|---|---|
| 8,641,977 B2 | 2/2014 | Snowball | |
| 8,685,329 B2 | 4/2014 | Lee | |
| 9,005,531 B2 | 4/2015 | Mole | |
| 9,034,255 B2 | 5/2015 | Lee | |
| 9,119,892 B2 | 9/2015 | Mueller et al. | |
| 9,370,592 B2 | 6/2016 | Lee | |
| 9,597,422 B2 | 3/2017 | Snowball | |
| 10,188,766 B2 | 1/2019 | Lee | |
| 10,232,076 B2 | 3/2019 | Lee | |
| 10,940,223 B2 | 3/2021 | Lee | |
| 10,967,094 B2 | 4/2021 | Lee | |
| 11,207,436 B2 | 12/2021 | Lee | |
| 2005/0099134 A1* | 5/2005 | Harada | H05H 1/2406 315/111.21 |
| 2005/0161433 A1 | 7/2005 | Silberberg et al. | |
| 2007/0119699 A1 | 5/2007 | Chambers et al. | |
| 2009/0041617 A1 | 2/2009 | Lee | |
| 2010/0047116 A1* | 2/2010 | Garner | A61L 2/10 422/4 |
| 2011/0212185 A1 | 9/2011 | Tanaka et al. | |
| 2012/0063959 A1 | 3/2012 | Woodbridge | |
| 2012/0093691 A1 | 4/2012 | Mole | |
| 2012/0111359 A1 | 5/2012 | Mueller et al. | |
| 2012/0148445 A1* | 6/2012 | Makoto | A61L 9/22 422/186 |
| 2012/0183444 A1 | 7/2012 | Lee | |
| 2012/0288405 A1 | 11/2012 | Snowball | |
| 2014/0065013 A1* | 3/2014 | Nonnenmacher | A61L 2/202 422/24 |
| 2014/0119991 A1 | 5/2014 | Snowball | |
| 2014/0154133 A1 | 6/2014 | Lee | |
| 2015/0196675 A1 | 7/2015 | Lee | |
| 2015/0273092 A1* | 10/2015 | Holub | B60Q 3/68 250/492.1 |
| 2015/0273093 A1* | 10/2015 | Holub | B60Q 3/68 250/492.1 |
| 2016/0287737 A1 | 10/2016 | Lee | |
| 2017/0144891 A1 | 5/2017 | Haruyama | |
| 2018/0185538 A1 | 7/2018 | Lee et al. | |
| 2019/0060500 A1 | 2/2019 | Lee | |
| 2019/0167832 A1 | 6/2019 | Lee | |
| 2019/0322107 A1* | 10/2019 | Ozawa | B41J 2/01 |
| 2021/0185793 A1* | 6/2021 | Wu | H01J 37/32348 |
| 2021/0187143 A1 | 6/2021 | Lee | |
| 2021/0308316 A1 | 10/2021 | Lee | |
| 2022/0072176 A1 | 3/2022 | Lee | |

FOREIGN PATENT DOCUMENTS

| | | | | | |
|---|---|---|---|---|---|
| CN | 103977439 | A | * | 8/2014 | |
| CN | 106390702 | A | | 2/2017 | |
| EP | 2411058 | B1 | | 5/2015 | |
| JP | S52-3872 | A | | 1/1977 | |
| JP | S64-25865 | A | | 1/1989 | |
| JP | S64-25866 | A | | 1/1989 | |
| JP | H10-328279 | A | | 12/1998 | |
| JP | H11-090370 | A | | 4/1999 | |
| JP | 3062251 | U | | 9/1999 | |
| JP | 2005-336492 | A | | 12/2005 | |
| JP | 2009-517175 | A | | 4/2009 | |
| JP | 2012-521240 | A | | 9/2012 | |
| JP | 2013-154145 | A | | 8/2013 | |
| JP | 2013-158706 | A | | 8/2013 | |
| JP | 2014-061418 | A | | 4/2014 | |
| JP | 2014-516013 | A | | 7/2014 | |
| JP | 2015-085297 | A | | 5/2015 | |
| JP | 2017-518948 | A | | 7/2017 | |
| KR | 10-1995-0014015 | | | 6/1995 | |
| KR | 10-2007-0039824 | A | | 4/2007 | |
| KR | 2017-0026482 | A | | 3/2017 | |
| KR | 101769806 | B1 | * | 8/2017 | A61L 2/02 |
| KR | 20180017425 | A | * | 2/2018 | B01D 53/86 |
| WO | 2010/032765 | A | | 3/2010 | |
| WO | 2015/198608 | A | | 12/2015 | |
| WO | 2017/110502 | A1 | | 6/2017 | |
| WO | 2017/183781 | A1 | | 10/2017 | |

OTHER PUBLICATIONS

Jul. 19, 2024 Extended Search Report in European Patent Application Pub. No. 21 832 011.7.
Jul. 31, 2024 Office Action in Korean Patent Application Pub. No. 10-2022-7044633.
Mar. 29, 2022 Office Action in Japanese Patent Application Pub. No. 2021-094894.
Dec. 21, 2021 Office Action in Japanese Patent Application Pub. No. 2021-094894.
International Search Report and Written Opinion of the International Searching Authority for International Patent Application No. PCT/JP2021/024666.
Apr. 26, 2024 Office Action in Chinese Patent Application Pub. No. 202180046623.0 (with English translation).
Jan. 16, 2025 Office Action in Korean Patent Application Pub. No. 10-2022-7044636.
Dec. 20, 2024 extended European Search Report European Patent Application No. 21 831 495.3.
Feb. 28, 2025 Office Action in Chinese Patent Application No. 202180046672.4 (with English translation).
Jul. 8, 2025 Office Action in Japanese Patent Application Pub. No. 2021-095018.
Apr. 28, 2025 Notice of Allowance in Korean Patent Application No. 10-2022-7044633.

* cited by examiner

STERILIZATION DEVICE, STERILIZATION METHOD, ACTIVE OXYGEN SUPPLY DEVICE, AND DEVICE FOR TREATMENT WITH ACTIVE OXYGEN

CROSS-REFERENCE TO RELATED APPLICATION

This is a continuation of International Application No. PCT/JP2021/024666, filed on Jun. 30, 2021, and designated the U.S., and claims priority from Japanese Patent Application No. 2020-113518 filed on Jun. 30, 2020, Japanese Patent Application No. 2020-176945 filed on Oct. 21, 2020, Japanese Patent Application No. 2021-074162 filed on Apr. 26, 2021, and Japanese Patent Application No. 2021-095018 filed on Jun. 7, 2021, the entire contents of which are incorporated herein by reference.

BACKGROUND OF THE INVENTION

Technical Field of the Invention

The present disclosure relates to a sterilization device and a sterilization method. Also, the present disclosure relates to an active oxygen supply device. Further, the present disclosure relates to a device for treatment with active oxygen.

Description of the Related Art

Ultraviolet light and ozone are known as means for sterilizing articles and the like. Japanese Patent Application Laid-open No. H01-25865 discloses a method using a sterilization device having an ozone supply device, an ultraviolet light generating lamp, and an agitating device to sterilize even the shaded portions of a sample by agitating active oxygen generated by irradiating ozone with ultraviolet light emitted by the ultraviolet light generating lamp, thereby solving the problem that sterilization by ultraviolet light is limited to a portion of an object to be sterilized that is irradiated with the ultraviolet light.

SUMMARY OF THE INVENTION

At least one aspect of the present disclosure is directed to providing a sterilization device and a sterilization method exhibiting superior sterilization performance that surpasses the sterilization performance of ozone and ultraviolet light. At least one aspect of the present disclosure is directed to an active oxygen supply device capable of actively supplying active oxygen to an object to be treated. Further, at least one aspect of the present disclosure is directed to a device for treatment with active oxygen that can more efficiently treat the surface of an object to be treated with active oxygen.

According to at least one aspect of the present disclosure, there is provided a sterilization device comprising a plasma generator and an ultraviolet light source, wherein the plasma generator is a plasma actuator that is provided with a first electrode and a second electrode with a dielectric in-between, and that generates an induced flow including ozone by applying a voltage between the two electrodes, the ultraviolet light source is arranged so as to be capable of irradiating a surface of an object to be treated, which is an object to be sterilized, and the plasma actuator is arranged so that the induced flow is supplied to the surface.

Also, according to at least one aspect of the present disclosure, there is provided a sterilization method comprising:

a step of providing an induced flow including ozone to a surface of an object to be treated, which is an object to be sterilized, the induced flow being generated by applying a voltage between a first electrode and a second electrode with a dielectric in-between; and a step of irradiating the induced flow including ozone that is supplied to the surface of the object to be treated with ultraviolet light.

Further, according to at least one aspect of the present disclosure, there is provided an active oxygen supply device comprising a plasma generator and an ultraviolet light source, wherein the plasma generator is a plasma actuator that is provided with a first electrode and a second electrode with a dielectric in-between, and that generates an induced flow including ozone by applying a voltage between the first electrode and the second electrode, the plasma actuator is arranged so that the induced flow is supplied to a surface of an object to be treated, and the ultraviolet light source irradiates the induced flow with ultraviolet light and generates active oxygen in the induced flow.

Moreover, according to at least one aspect of the present disclosure, there is provided a device for treatment with active oxygen comprising a plasma generator and an ultraviolet light source, wherein the plasma generator is a plasma actuator that is provided with a first electrode and a second electrode with a dielectric in-between, and that generates an induced flow including ozone by applying a voltage between the first electrode and the second electrode, the plasma actuator is arranged so that the induced flow is supplied to a surface of an object to be treated, and the ultraviolet light source irradiates the induced flow with ultraviolet light and generates active oxygen in the induced flow.

According to one embodiment of the present disclosure, it is possible to obtain a sterilization device exhibiting superior sterilization performance that surpasses the sterilization performance of ozone and ultraviolet light. Further, according to another embodiment of the present disclosure, it is possible to obtain a sterilization method that exhibits excellent sterilization performance exceeding the sterilization performance of a sterilization method using ozone or ultraviolet light.

Further, according to one embodiment of the present disclosure, it is possible to obtain an active oxygen supply device capable of more actively supplying active oxygen to the object to be treated.

Furthermore, according to another embodiment of the present disclosure, it is possible to obtain a device for treatment with active oxygen that is capable of more efficiently treating the surface of an object to be treated with active oxygen.

Further features of the present invention will become apparent from the following description of exemplary embodiments with reference to the attached drawings.

DESCRIPTION OF THE EMBODIMENTS

Figure 1:
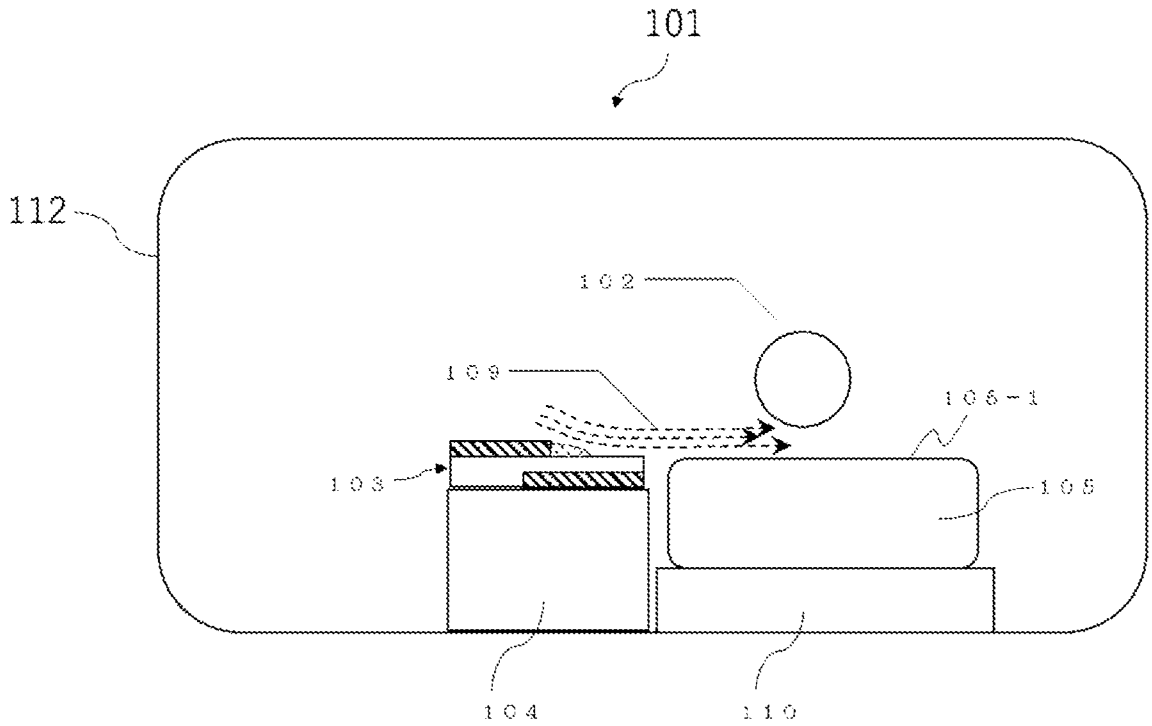
FIG. 1 is a schematic drawing showing the configuration of a sterilization device according to one embodiment of the present disclosure.

Hereinafter, specific examples of embodiments for carrying out the present disclosure will be described with reference to the drawings. However, the dimensions, materials, shapes, and relative arrangement of the components described in the embodiments should be changed, as appropriate, according to the configuration of the members to which the disclosure is applied and various conditions. That is, the scope of the present disclosure is not intended to be limited to the following embodiments.

In addition, in the present disclosure, the descriptions of "XX or more and YY or less" or "XX to YY" representing numerical ranges mean numerical ranges including the lower and upper limits, which are endpoints, unless otherwise specified. When numerical ranges are stated stepwise, the upper and lower limits of each numerical range can be combined arbitrarily.

Further, "bacteria" in "sterilization" according to the present disclosure refers to microorganisms, and the microorganisms include fungi, bacteria, unicellular algae, viruses, protozoa, and the like, as well as animal or plant cells (stem cells, dedifferentiated cells and differentiated cells), tissue cultures, fused cells obtained by genetic engineering (including hybridomas), dedifferentiated cells, and transformants (microorganisms). Examples of viruses include, for example, norovirus, rotavirus, influenza virus, adenovirus, coronavirus, measles virus, rubella virus, hepatitis virus, herpes virus, HIV virus, and the like. Examples of bacteria include *Staphylococcus, Escherichia coli, Salmonella, Pseudomonas aeruginosa, Vibrio cholerae, Shigella*, Anthrax, *Mycobacterium tuberculosis, Clostridium botulinum*, Tetanus, *Streptococcus*, and the like. Furthermore, examples of fungi include *Trichophyton, Aspergillus, Candida*, and the like.

Furthermore, in the following explanation, configurations having the same functions are given the same numbers in the drawings, and description thereof may be omitted.

Furthermore, in the present description, the active oxygen supply device of the present disclosure and the device for treatment with active oxygen of the present disclosure are collectively referred to simply as "active oxygen supply device".

When the present inventors studied the sterilization performance of the sterilization method according to Japanese Patent Application Laid-open No. H01-25865, there were cases where the sterilization performance was about the same as that of the conventional sterilization method using only ozone. Since it is said that the sterilization ability of active oxygen is intrinsically far superior to that of ozone, such a study result was unexpected.

According to the study of the present inventors, the reason why the sterilization ability of the sterilization device according to Japanese Patent Application Laid-open No. H01-25865 is limited is presumed to be as follows.

In Japanese Patent Application Laid-open No. H01-25865, ozone is excited by irradiation with ultraviolet light to generate active oxygen with extremely high sterilization power. Here, active oxygen is a general term for highly reactive oxygen active species such as superoxide anion radicals ($.O_2$—) and hydroxyl radicals (.OH). Due to high own reactivity thereof, active oxygen can instantly oxidize and decompose bacteria and viruses.

However, since ozone absorbs ultraviolet light very well, in the sterilization device according to Japanese Patent Application Laid-open No. H01-25865, generation of active oxygen is considered to be limited to the vicinity of the ultraviolet light generating lamp. That is, it is considered that the ultraviolet light does not sufficiently reach the ozone present at a position distant from the ultraviolet light generating lamp, and active oxygen is hardly generated at a position distant from the ultraviolet light generating lamp.

In addition, active oxygen is extremely unstable, with a half-life of $10^{-6}$ sec for $.O_2^-$ and a half-life of $10^{-9}$ sec for .OH, which are rapidly converted into stable oxygen and water. Therefore, it is difficult to fill the inside of the body of a sterilization device with active oxygen generated in the vicinity of an ultraviolet light generating lamp, and it is considered difficult to significantly sterilize with active oxygen unless an object to be sterilized is placed at a position very close to an ultraviolet light generating lamp, for example, within about 1 cm from the ultraviolet light generating lamp. In other words, when an object to be sterilized is present at a distance of 1 cm or more from the ultraviolet light generating lamp, it is considered that the sterilization of the object to be sterilized is substantially performed by ozone. Therefore, it is considered that the sterilization performance of the sterilization method according to Japanese Patent Application Laid-open No. H01-25865 is about the same as the sterilization performance of the conventional sterilization method using only ozone.

Based on these considerations, the present inventors have recognized that when treating an object to be treated using active oxygen, which has a short life, it is necessary to place the object to be treated and the surface to be treated more actively in an active oxygen atmosphere. As a result of studies conducted by the present inventors under such recognition, it was found that the object to be treated can be more actively placed in the active oxygen atmosphere by using the sterilization device and the active oxygen supply device of the embodiments described below. In the present disclosure, the "treatment" of the object to be treated with active oxygen is inclusive of various types of treatment that can be accomplished by active oxygen, such as surface modification (hydrophilization treatment) sterilization, deodorization, bleaching, and the like of the surface of the object to be treated with active oxygen.

FIG. 1 shows a sterilization device 101 according to one embodiment of the present disclosure. The sterilization device 101 includes an ultraviolet light source 102 and a plasma generator 103 inside a sterilization container 112.

The ultraviolet light source 102 is arranged so as to be capable of irradiating a treatment surface 105-1 of an object 105 to be treated, which is an object to be sterilized, that is placed on a mounting table 110. In FIG. 1, reference numeral 109 denotes an induced flow.

Figure 2:
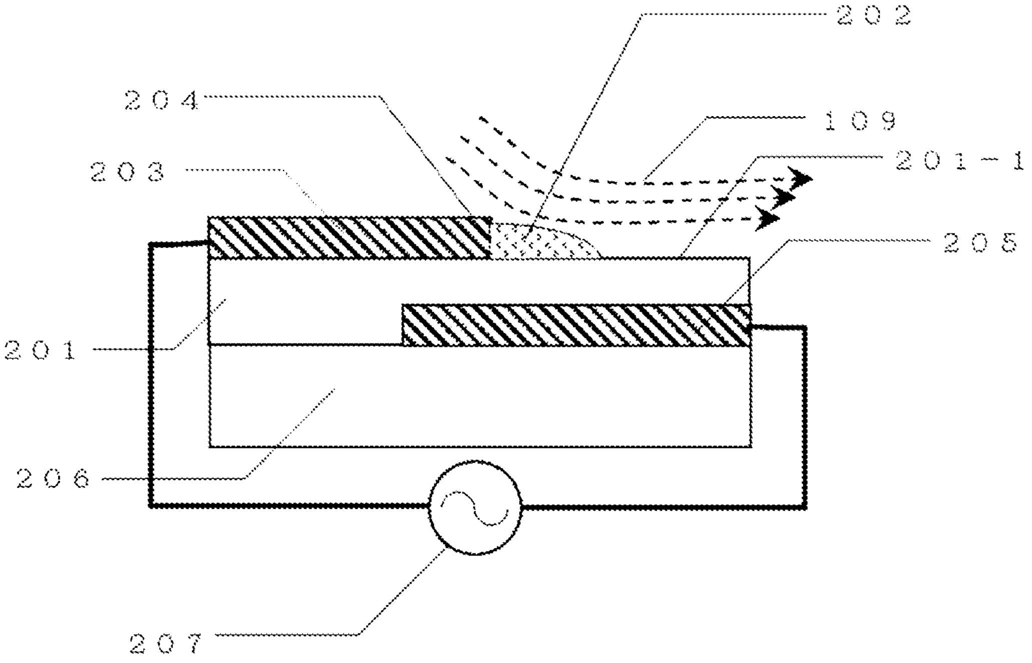
FIG. 2 is a schematic drawing showing an example of the configuration of a plasma generator.

A cross-sectional structure of one embodiment of the plasma generator 103 is shown in FIG. 2. The plasma generator is a so-called dielectric barrier discharge (DBD) plasma actuator (hereinafter sometimes simply referred to as "DBD-PA") in which a first electrode 203 is provided on one surface (hereinafter referred to as "first surface") of a dielectric 201 and a second electrode 205 provided on a surface (hereinafter referred to as "second surface") opposite to the first surface. In FIG. 2, reference numeral 206 denotes a dielectric substrate, and reference numeral 207 denotes a power source.

In the plasma generator 103, the first electrode 203 and the second electrode 205, which are arranged with the dielectric 201 interposed in-between, are obliquely arranged with a shift. By applying a voltage between these electrodes (between both electrodes), plasma 202 is generated from the first electrode 203 toward the second electrode 205, and a jet-like flow is induced by the surface plasma 202 from an edge 204 of the first electrode 203 along the exposed portion (the portion not covered with the first electrode) 201-1 of the first surface of the dielectric 201. At the same time, a suction flow of air is generated from the space within the container toward the electrodes. Electrons in the surface plasma 202 collide with oxygen molecules in the air thereby causing dissociation of the oxygen molecules and producing oxygen atoms. The generated oxygen atoms collide with undissociated oxygen molecules to generate ozone. Therefore, due to the action of the jet-like flow created by the surface plasma 202 and the suction flow of air, an induced flow 109 including high-concentration ozone is generated from the edge 204 of the first electrode 203 along the surface of the dielectric 201.

The plasma generator 103 is arranged on the mounting table 104 so that the induced flow 109 is supplied to the treatment surface 105-1 of the object 105 to be treated that is irradiated with the ultraviolet light from the ultraviolet light source 102.

That is, in the sterilization device according to one embodiment of the present disclosure, the induced flow 109 including ozone from the plasma generator 103 is supplied to the treatment surface 105-1 of the object 105 to be treated, thereby making it possible to increase locally the ozone concentration in the region close to the treatment surface 105-1, specifically, for example, in the spatial region up to a height of about 1 mm from the treatment surface 105-1 (hereinafter referred to as "surface region"). Therefore, it is not necessary to increase the ozone concentration in the space from the ultraviolet light source 102 to the surface region, and it is possible to prevent ultraviolet light from attenuating before reaching the surface region. As a result, ozone present in the surface region is efficiently decomposed into active oxygen by ultraviolet light. Furthermore, as a result, active oxygen is generated on the treatment surface 105-1 of the object to be treated or at a position very close to the treatment surface 105-1. As a result, the treatment surface 105-1 of the object 105 to be treated is placed in an active oxygen atmosphere generated in situ on the treatment surface, and the treatment surface is more reliably sterilized by the active oxygen.

<Electrodes and Dielectric>

The material constituting the first electrode and the second electrode is not particularly limited as long as it is a highly conductive material. For example, metals such as copper, aluminum, stainless steel, gold, silver, and platinum, materials plated or vapor-deposited therewith, conductive carbon materials such as carbon black, graphite, and carbon nanotubes, composite materials which are mixtures thereof with resins and the like can be used. The materials forming the first electrode and the material forming the second electrode may be the same or different.

Among these, from the viewpoint of avoiding electrode corrosion and achieving uniform discharge, it is preferable that the material constituting the first electrode be aluminum, stainless steel, or silver. For the same reason, the material constituting the second electrode is also preferably aluminum, stainless steel, or silver.

In addition, the shape of the first electrode and the second electrode can be plate-like, wire-like, needle-like, or the like, without particular limitation. Preferably, the shape of the first electrode is flat. Further, preferably, the shape of the second electrode is flat. When at least one of the first electrode and the second electrode is flat, the flat plate preferably has an aspect ratio (long side length/short side length) of 2 or more.

At least one of the first electrode and the second electrode preferably has an apex angle of 45° or less (that is, the electrode is sharp), but this feature is not limiting. Although the drawings show the case where the apex angles of the first electrode and the second electrode are both 90°, the present disclosure is also inclusive of an embodiment in which the apex angle exceeds 45°.

The dielectric is not particularly limited as long as it is a material with high electrical insulation. For example, resins such as polyimides, polyesters, fluororesins, silicone resins, acrylic resins, and phenolic resins, glass, ceramics, and composite materials which are mixtures thereof with resins can be used. Among these, ceramics and glass are preferable because they can further increase the electric field strength.

<Plasma Actuator>

The plasma actuator is not particularly limited as long as an induced flow including ozone can be generated by providing a first electrode and a second electrode with a dielectric disposed in-between and applying a voltage between the electrodes. In the plasma actuator, the shorter the shortest distance between the first electrode and the second electrode, the easier plasma is generated. Therefore, the thickness of the dielectric is preferably as small as possible as long as no electrical breakdown occurs, and can be 10 μm to 1000 μm, preferably 10 μm to 200 μm. Also, the shortest distance between the first electrode and the second electrode is preferably 200 μm or less.

Figure 3:
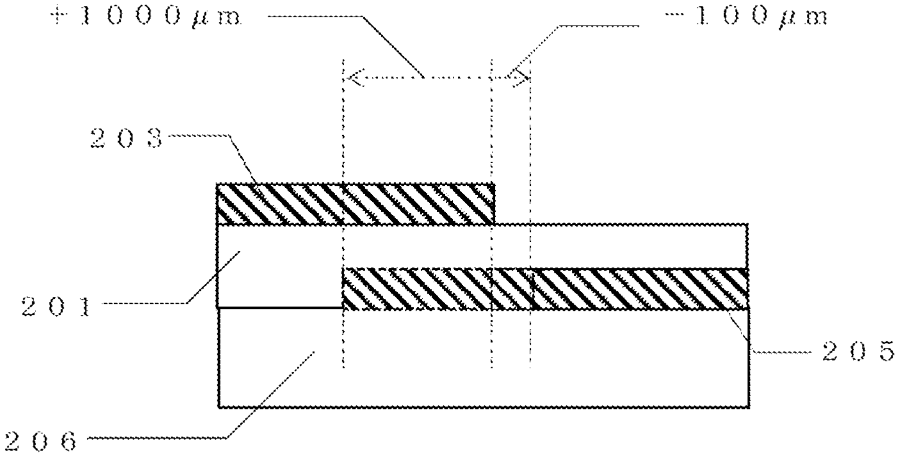
FIG. 3 is an explanatory drawing illustrating overlapping between the first electrode and the second electrode.

FIG. 3 is an explanatory diagram of the overlap between the first electrode 203 and the second electrode 205 of the plasma actuator, which is an ozone generator. This is a cross-sectional view of the plasma actuator.

In the first electrode 203 and the second electrode 205 arranged obliquely opposite each other, the edge of the first electrode may be present at the portion where the second electrode is formed with the dielectric disposed in-between, when viewed from the upper side of the cross-sectional view. That is, the first electrode and the second electrode may be provided so as to overlap each other with the dielectric disposed in-between. In this case, it is preferable to prevent dielectric breakdown at the time of voltage application in the portion where the first electrode and the second electrode overlap each other with the dielectric disposed in-between.

Also, when the first electrode and the second electrode are separated from each other when viewed from the top of the cross-sectional view, it is preferable to increase the voltage in order to compensate for the weakening of the electric field due to the increased distance between the electrodes. The overlap between the edge of the first electrode and the edge of the second electrode is more preferably −100 μm to +1000

μm when viewed from the top of the cross-sectional view, assuming that the overlapping length is positive.

The thickness of the electrodes is not particularly limited for both the first electrode and the second electrode and can be 10 μm to 1000 μm. When the thickness is 10 μm or more, the resistance becomes low and plasma is easily generated. When the thickness is 1000 μm or less, electric field concentration is likely to occur, and plasma is likely to be generated.

The width of the electrodes is not particularly limited for both the first electrode and the second electrode and can be 1000 μm or more.

Further, when the edge of the second electrode is exposed, plasma is also generated from the edge of the second electrode, and an induced flow is generated in the opposite direction to the induced flow 109 originating from the first electrode. In the sterilization device according to the present embodiment, it is preferable to keep the ozone concentration in the inner space of the sterilization container other than the surface region of the object to be treated as low as possible. Moreover, it is preferable not to generate a gas flow in the container that disturbs the flow of the induced flow 109. Therefore, it is preferable not to generate an induced flow originating from the second electrode. Accordingly, it is preferable to cover the second electrode 205 with a dielectric such as the dielectric substrate 206 as shown in FIGS. 2 and 3 or embed the second electrode in the dielectric 201 to prevent plasma generation from the edges of the second electrode.

The induced flow 109 including high-concentration ozone flows in the direction of jet-like flow induced by surface plasma from the edge 204 of the first electrode 203 along the exposed portion 201-1 of the first surface of the dielectric 201, that is, in the direction from the edge 204 of the first electrode 203 along the exposed portion 201-1 of the first surface of the dielectric. This induced flow is a flow of gas including high-concentration ozone and having a velocity of several m/s to several tens of m/s.

The voltage applied between the first electrode 203 and the second electrode 205 of the plasma actuator is not particularly limited as long as plasma can be generated in the plasma actuator. Further, the voltage may be a DC voltage or an AC voltage, but an AC voltage is preferred. Moreover, in a preferable embodiment, the voltage is a pulse voltage.

Further, the amplitude of the voltage can be 1 kV to 100 kV. Furthermore, the frequency of the voltage is preferably 1 kHz or higher, more preferably 10 kHz to 100 kHz. When the voltage is an alternating voltage, the waveform of the alternating voltage is not particularly limited, and a sine wave, a rectangular wave, a triangular wave, or the like can be used, but a rectangular wave is preferable from the viewpoint of the rapid rise of the voltage.

The duty ratio of the voltage can also be selected as appropriate, but it is preferable that the voltage rises quickly. Preferably, the voltage is applied so that the rise of the voltage from the bottom to the peak of the amplitude of the wavelength is 4,000,000 V/sec or more.

The value obtained by dividing the amplitude of the voltage applied between the first electrode 203 and the second electrode 205 by the film thickness of the dielectric 201 (voltage/film thickness) is preferably 10 kV/mm or more.

<Ultraviolet Light Source and Ultraviolet Light>

The ultraviolet light source is not particularly limited as long as ultraviolet light that can excite ozone and generate active oxygen can be emitted. However, since the peak value of the light absorption spectrum of ozone is 260 nm, the peak wavelength of the ultraviolet light is preferably 220 nm to 310 nm, more preferably 253 nm to 285 nm, and even more preferably 253 nm to 266 nm.

Examples of specific ultraviolet light sources that can be used include low-pressure mercury lamps in which mercury is enclosed in quartz glass together with an inert gas such as argon or neon, cold cathode tube ultraviolet lamps (UV-CCL), ultraviolet LEDs, and the like. The wavelength of the low-pressure mercury lamp and the cold-cathode tube ultraviolet lamp may be selected from 254 nm or the like. Meanwhile, the wavelength of the ultraviolet LED may be selected from 265 nm, 275 nm, 280 nm, and the like from the viewpoint of output performance.

<Arrangement of Plasma Generator, Ultraviolet Light Source and Object to Be Treated>

The position of the plasma generator 103 that generates the induced flow including ozone in the sterilization container 112 is arranged so that the induced flow 109 including ozone is supplied to the treatment surface 105-1 of the object to be treated, which is the object to sterilized, in order to increase the ozone concentration in the surface region of the object to be treated.

For example, the plasma generator and the object to be treated may be arranged so that the induced flow 109 containing high-concentration ozone is supplied to the surface of the object to be treated in the shortest distance.

Also, for example, the treatment surface 105-1 of the object to be treated may be arranged to be included on an extension line in the direction along the exposed portion 201-1 of the first surface of the dielectric from the edge of the first electrode of the plasma actuator.

Further, the angle (plasma actuator incident angle, also referred to as PA incident angle) between an extension line of the direction from the edge of the first electrode of the plasma actuator along the exposed portion 201-1 of the first surface of the dielectric and the treatment surface 105-1 of the object to be treated is preferably 0° to 45°, more preferably 0° to 30°.

By arranging the plasma generator and the object to be treated as described above, an induced flow including ozone and having a certain flow velocity can be locally supplied to a region near the surface of the object to be treated.

The ultraviolet light source is not particularly limited as long as the arrangement thereof is such that the surface of the object to be treated, which is the object to be sterilized, can be irradiated.

As described above, since the induced flow including ozone is supplied to the area near the surface of the object to be treated, the ozone concentration near the surface can be locally increased. Therefore, the ultraviolet light from the ultraviolet light source can be prevented from being absorbed and attenuated by ozone before reaching the surface region. As a result, the ozone present in the surface region is efficiently decomposed into active oxygen by the ultraviolet light.

The distance between the ultraviolet light source and the object to be treated is preferably 3 cm or less, more preferably 1 cm or less. However, it is not necessary to place the object to be treated at a location within about 1 cm from the ultraviolet light source, and a single device can sterilize the surfaces of objects to be treated having various sizes and thicknesses.

In another preferred embodiment, a moving means for the ultraviolet light source and/or the object to be treated is provided so that the ultraviolet light source and/or the object to be treated be movable to ensure uniform illuminance.

Further, the angle formed between the extension line in the direction from the edge of the first electrode of the plasma actuator along the surface of the dielectric with ultraviolet light emitted from the ultraviolet light source, with the object to be treated as the vertex, is preferably 45° to 180°. Where the angle is 45° to 180°, UV light and ozone can be prevented from producing active oxygen before reaching the object to be treated, and the sterilization effect is further improved.

Furthermore, at the intersection of the extension line in the direction from the edge of the first electrode along the surface of the dielectric of the plasma actuator and the ultraviolet light emitted from the ultraviolet light source (that is, at the position of the ultraviolet light from the ultraviolet light source corresponding to the surface of the object to be treated), the illuminance is preferably 100 $\mu W/cm^2$ or more. In addition, at the intersection of the extension line in the direction from the edge of the first electrode along the surface of the dielectric of the plasma actuator and the ultraviolet light emitted from the ultraviolet light source (that is, at the position of the ultraviolet light from the ultraviolet light source corresponding to the surface of the object to be treated), it is preferable to generate an induced flow with an ozone concentration of 20 ppm or more.

Figure 6:
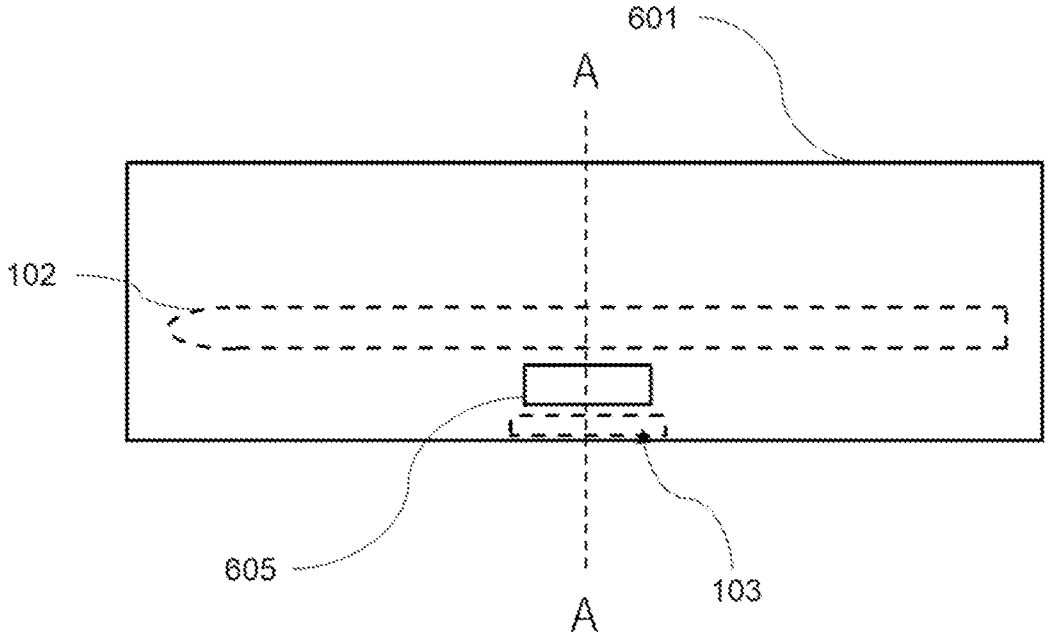
FIG. 6 is a schematic drawing showing the configuration of the active oxygen supply device according to one embodiment of the present disclosure, the plan view being taken from the side of a housing having an opening.
Figure 7:
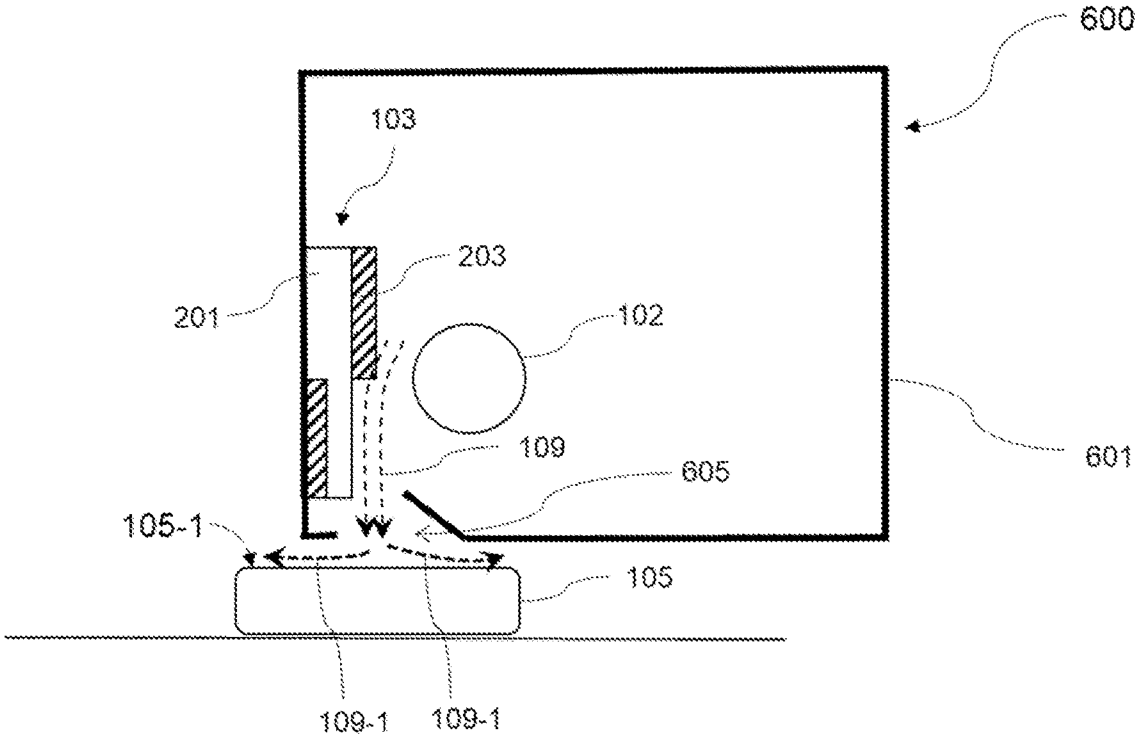
FIG. 7 is a cross-sectional view taken along line AA in the active oxygen supply device shown in FIG. 6.
Figure 8:
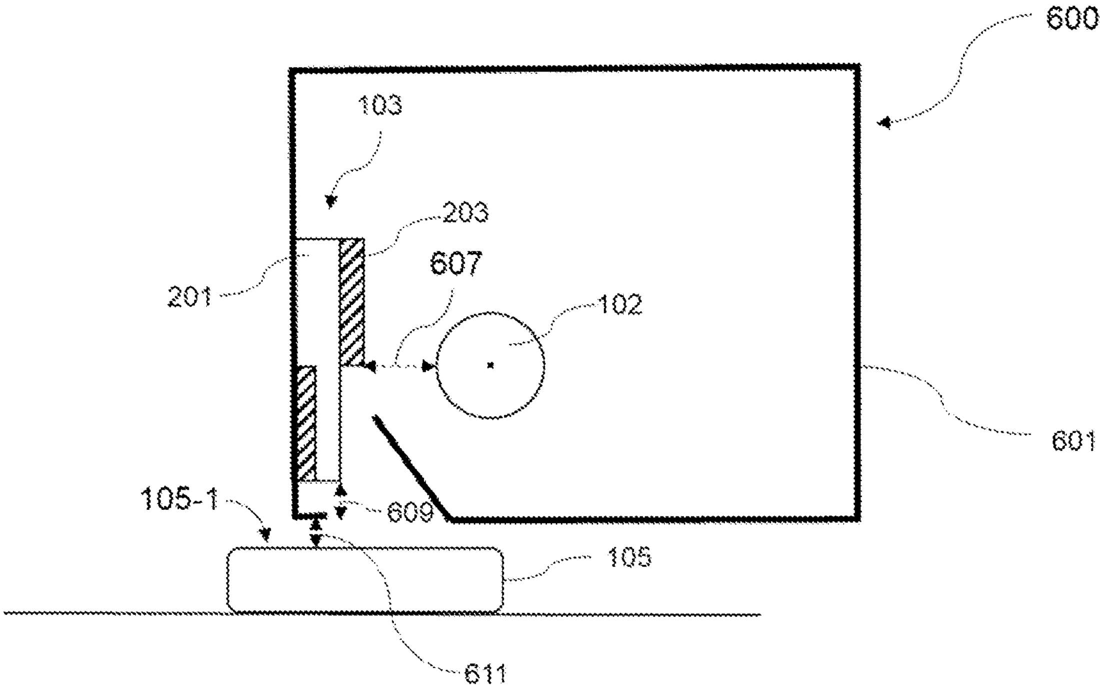
FIG. 8 is an explanatory drawing of the active oxygen supply device shown in FIG. 6.

FIGS. 6 to 8 show the configuration of an active oxygen supply device 600 according to one embodiment of the present disclosure.

Reference numerals 102, 103, 105, 105-1, and 109 in FIGS. 6 to 8 are the same as those in FIG. 1. The active oxygen supply device according to FIGS. 6 to 8 comprises a housing 601 having at least one opening 605, and the ultraviolet light source 102 and the plasma actuator 103 are arranged inside the housing. The plasma actuator 103 is arranged so that the induced flow 109 including ozone from the plasma actuator flows out of the housing through the opening 605. The ultraviolet light source 102 is arranged so that the induced flow 109 is irradiated with the ultraviolet light emitted from the ultraviolet light source. In the induced flow irradiated with ultraviolet light, the ozone in the induced flow is excited and contains active oxygen. As a result, the induced flow including active oxygen flows out from the opening. At this time, by arranging the object 105 to be treated in contact with the opening, the active oxygen is actively supplied to the surface 105-1 to be treated, and the surface to be treated can be actively placed in an active oxygen atmosphere. In addition, by arranging the object 105 to be treated near the opening, the induced flow flowing out of the opening flows along the surface of the object to be treated (see reference numeral 109-1 in FIG. 7). A part of the surface to be treated other than the part facing the opening is also exposed to the induced flow including active oxygen. As a result, a wider range of the surface 105-1 to be treated can be treated with active oxygen. The above description refers to the plasma actuator according to this embodiment, the electrodes and dielectrics used therein, and the ultraviolet light source and ultraviolet light.

Here, the intensity of the ultraviolet light source and the position thereof with respect to the plasma generator may be set such that the induced flow is irradiated with light including ultraviolet light to generate active oxygen in the induced flow, and the induced flow including an effective amount of active oxygen corresponding to the purpose of the treatment can be supplied to the object to be treated through the opening. As an example of the arrangement position of the ultraviolet light source with respect to the plasma actuator, for example, it is preferable that the distance from the surface of the dielectric of the plasma actuator facing the ultraviolet light source be 10 mm or less, particularly 4 mm or less. As an example of the intensity of light including ultraviolet light, for example, the illuminance on the surface of the dielectric of the plasma actuator facing the ultraviolet light source is preferably 40 $\mu W/cm^2$ or more, particularly 100 $\mu W/cm^2$ or more. Although the upper limit of the illuminance is not particularly limited, it is preferably, for example, 10,000 $\mu W/cm^2$ or less.

Furthermore, as for the distance between the plasma actuator and the opening, it is preferable that the distance between the plasma actuator and the object to be treated be short in order to use the active oxygen in the induced flow more effectively for the desired treatment. Therefore, it is preferable to arrange the plasma actuator at a position closer to the opening. Meanwhile, in order to protect the plasma actuator, it is also preferable to arrange the plasma actuator at a position set back from the opening. For example, the plasma actuator is preferably arranged on the inner wall of the housing such that the end portion of the plasma actuator on the side close to the opening be located at a distance of 0.5 mm to 1.5 mm from the edge of the opening on the inner wall of the housing.

Furthermore, in the active oxygen supply device according to the present embodiment, the positions of the plasma generator 103 and the ultraviolet light source 102 that generate the induced flow including ozone are not particularly limited as long as active oxygen is generated in the induced flow by light including ultraviolet light from the ultraviolet light source, and the induced flow including an effective amount of active oxygen corresponding to the purpose of the treatment flows out from the opening and is supplied to the surface to be treated.

In the present embodiment, the flow velocity of the induced flow from the opening is not particularly limited as long as the induced flow including an effective amount of active oxygen is supplied to the surface to be treated according to the distance of the object to be treated from the opening and the purpose of the treatment. As an example, for example, when the plasma actuator is arranged within the housing so that the end portion of the plasma actuator on the side close to the opening is located at a distance of 0.5 mm to 1.5 mm from the edge of the opening on the inner wall of the housing, as described hereinabove, and the surface to be treated of the object to be treated is positioned with respect to the object to be treated so that the distance from the surface of the housing having the opening is 0.5 mm to 2 mm, the preferred flow velocity of the induced flow in the opening is 0.01 m/s to 100 m/s. Such flow velocity can be adjusted by the dielectric material and voltage conditions applied to the electrodes of the plasma actuator. As for the dielectric, the higher the volume resistivity, the stronger the electric field strength can be made, and as a result, the higher the velocity of the induced flow from the plasma actuator can be made. Therefore, ceramics such as glass are more preferably used as the dielectric, as described above. Further, preferable voltage conditions are as described above.

In the active oxygen supply device according to FIGS. 6 to 8, the housing is configured so that the surface to be treated is not directly irradiated with ultraviolet light, but a configuration in which the surface to be treated is directly irradiated falls under the category of modified examples of the present embodiment. In this case, since active oxygen can also be generated in-situ on the surface to be treated, further improvement in the efficiency of treatment of the surface to be treated can be expected.

Here, in the sterilization treatment using only ultraviolet light, only the surface irradiated with ultraviolet light is sterilized. However, in the sterilization treatment by the active oxygen supply device according to the present disclosure, it is possible to sterilize the bacteria present at the position where the active oxygen can reach. Therefore, for example, even bacteria present between fibers, which are difficult to sterilize by external ultraviolet irradiation, can be sterilized.

EXAMPLES

The present disclosure will be described in more detail below using Examples and Comparative Examples, but the embodiments of the present disclosure are not limited to these.

Example 1

1. Production of Sterilization Device

The first electrode was formed by attaching an aluminum foil having a length of 18 mm, a width of 9.5 mm, and a thickness of 100 μm to the first surface of a glass plate (length 18 mm, width 18 mm, thickness 150 μm) as a dielectric with a pressure-sensitive adhesive tape so that a region of the first surface of the glass plate having a length of 18 mm and a width of 3 mm was exposed. Further, the second electrode was formed by attaching an aluminum foil having a length of 18 mm, a width of 9 mm, and a thickness of 100 μm to the second surface of the glass plate with a pressure-sensitive adhesive tape so as to obliquely face the aluminum foil attached to the first surface. Additionally, the second side, including the second electrode, was covered with a polyimide tape. In this way, a plasma actuator was produced in which the first electrode and the second electrode were provided so as to overlap each other over a width of 0.5 mm with the dielectric (glass plate) disposed in-between.

Figure 4A:
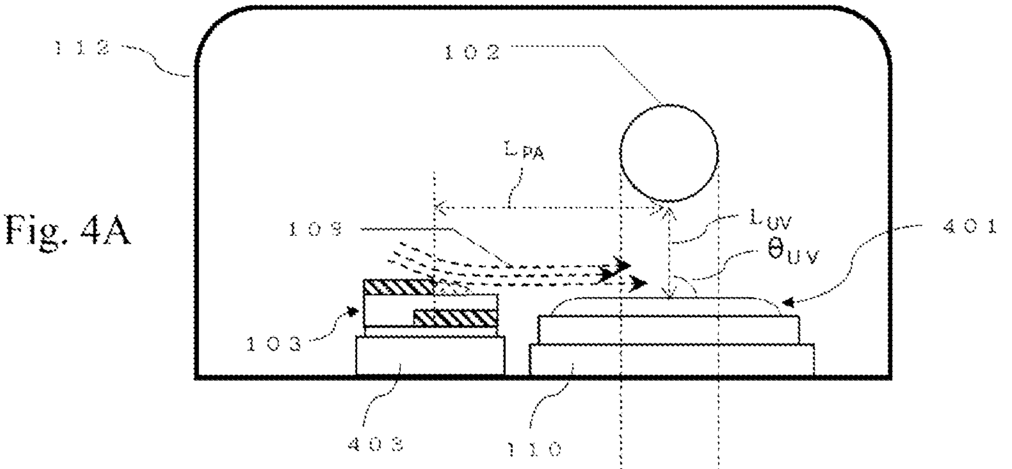
FIG. 4A is a schematic cross-sectional view of the sterilization device according to the present example.
Figure 4B:
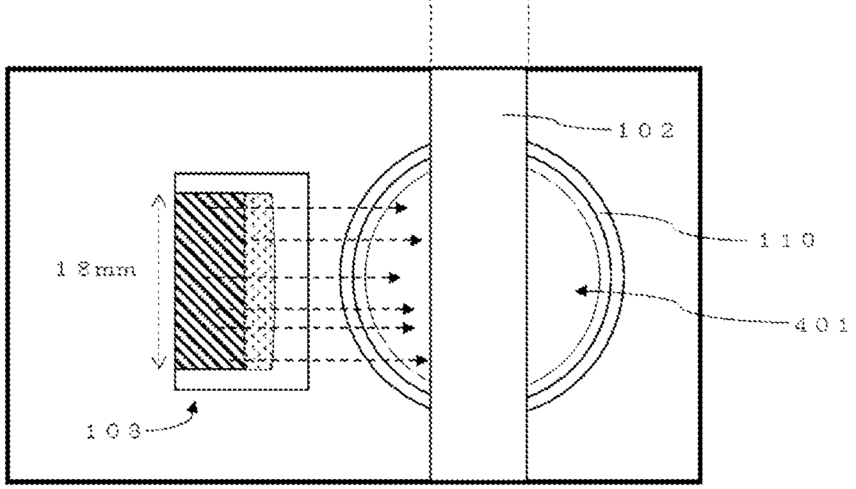
FIG. 4B is a plan view of the same.

As shown in FIG. 4A and FIG. 4B, this plasma actuator was placed on a mounting table 403 inside a sterilization container 112 having a length of 15 cm, a width of 10 cm, and a height of 7 cm so that the first electrode faced vertically upward and also so that the surface (201-1) of the glass plate on which the first electrode was formed and which was not covered by the first electrode was horizontal. FIG. 4A is a schematic cross-sectional view of the sterilization device according to this example, and FIG. 4B is a plan view.

In addition, a mounting table 110 for the object to be sterilized was arranged inside the sterilization device. The mounting table 110 was arranged at a position such that the distance between the end portion of the first electrode and the center of the object to be treated (LPA in FIG. 4A) was 5 cm and so that the surface to be treated of an evaluation sample, which is described hereinbelow, was horizontal and flush with the surface of the dielectric of the plasma actuator 103 on which the first electrode was formed and which was not covered by the first electrode.

Furthermore, a cold-cathode tube ultraviolet lamp (trade name: UW/9F89/9, manufactured by Stanley Electric Co., Ltd., peak wavelength=254 nm) was prepared as an ultraviolet light source. The lamp was arranged inside the sterilization container at a position such that the distance between the surface to be treated and the cold-cathode tube ultraviolet lamp (LUV in FIG. 4A) was 3 cm and the incident angle of the ultraviolet light to the center position of the surface to be treated (θUV in FIG. 4A) was 90°.

For this sterilization device, an illuminance meter (trade name: spectral irradiance meter USR-45D, manufactured by Ushio Inc.) was placed at the position of the surface to be treated when the evaluation sample was placed on the mounting table, and the illuminance of the ultraviolet light was measured. The integrated value of the spectrum was 487 $\mu W/cm^2$.

Furthermore, 5 min after applying a voltage having a sine waveform with an amplitude of 2.4 kV and a frequency of 80 kHz to the plasma actuator, 50 ml of gas was sampled from the position of the surface to be treated when the sample for evaluation was placed on the mounting table. The sampled gas was sucked into an ozone detection tube (trade name: 182SB, manufactured by Komyo Rikagaku Kogyo K.K.), and the concentration of ozone contained in the induced flow from the plasma actuator was measured to be 40 ppm (read value×2). In addition, 50 ml of gas was sampled at the midpoint (LUV/2) between the position of the surface to be treated and the ultraviolet light source, and the sampled gas was sucked into an ozone detection tube (trade name: 182SB, manufactured by Komyo Rikagaku Kogyo K. K.). The ozone concentration was measured to be 8 ppm (read value×2).

2. Preparation of Samples for Evaluation

A stamp medium (trade name: PETAN CHECK 25 PT1025 manufactured by Eiken Chemical Co., Ltd.) was pressed for 10 sec under a pressure of 25 $g/cm^2$ against a door knob that had not been wiped with water, alcohol, etc. for a week in a location where an unspecified number of people entered and exited, and then the stamp medium was allowed to stand for 12 h in an environment at a temperature of 37° C. A colony grown in the stamp medium was collected using a sterile cotton swab and dispersed in distilled water to prepare a bacterial solution. A new stamp medium (PETAN CHECK 25 PT1025 manufactured by Eiken Chemical Co., Ltd.) was smeared with 0.1 ml of a diluted bacterial solution obtained by diluting this bacterial solution 10-fold with distilled water, and was allowed to stand for 12 h in an environment at a temperature of 37° C. As a result, growth of bacteria of 200 CFU/ml to 300 CFU/ml was confirmed.

Thus, a sample for evaluation was prepared by smearing 0.1 ml of the diluted bacterial solution on a new stamp medium (PETAN CHECK 25 PT1025 manufactured by Eiken Chemical Co., Ltd.).

3. Sterilization Test

An evaluation sample 401 produced in Section 2 hereinabove was placed on the mounting table 110 of the sterilization device produced in Section 1 hereinabove. Next, a voltage having a sine waveform with an amplitude of 2.4 kV and a frequency of 80 kHz was applied to the plasma actuator, and sterilization treatment was performed by irradiating with ultraviolet light for 5 min. After that, the evaluation sample was taken out from the sterilization device and cultured at a temperature of 37° C. for 12 h. The number of surviving bacteria was calculated from the number of colonies grown on the medium. The sterilization test was performed three times, and the average value multiplied by 10 was used as the number of colonies in the sterilization test according to the present example. Based on the number of colonies obtained, the sterilization performance was evaluated according to the following criteria (Ten Cate determination display method).

−: No growth

±: Number of colonies<10

+: Number of colonies 10 to 29

++: Number of colonies 30 to 100

+++: Number of colonies>100

++++: Countless colonies

Examples 2 to 5

A sterilization device was produced and evaluated in the same manner as in Example 1, except that the ultraviolet light source and the thickness of the dielectric of the plasma actuator were changed as shown in Table 1. In Example 2, an ultraviolet LED (peak wavelength: 280 nm) was used as the ultraviolet light source.

Comparative Examples 1 to 3

The conditions for Comparative Examples 1 to 3 were the same as those for Example 1, except that the following changes were made.

Comparative Example 1: No voltage was applied to the plasma actuator, and no ultraviolet light irradiation was performed.

Comparative Example 2: Ultraviolet light irradiation was performed for 5 min without applying voltage to the plasma actuator.

Comparative Example 3: A voltage was applied to the plasma actuator for 5 min without ultraviolet light irradiation.

Comparative Example 4

Figure 5:
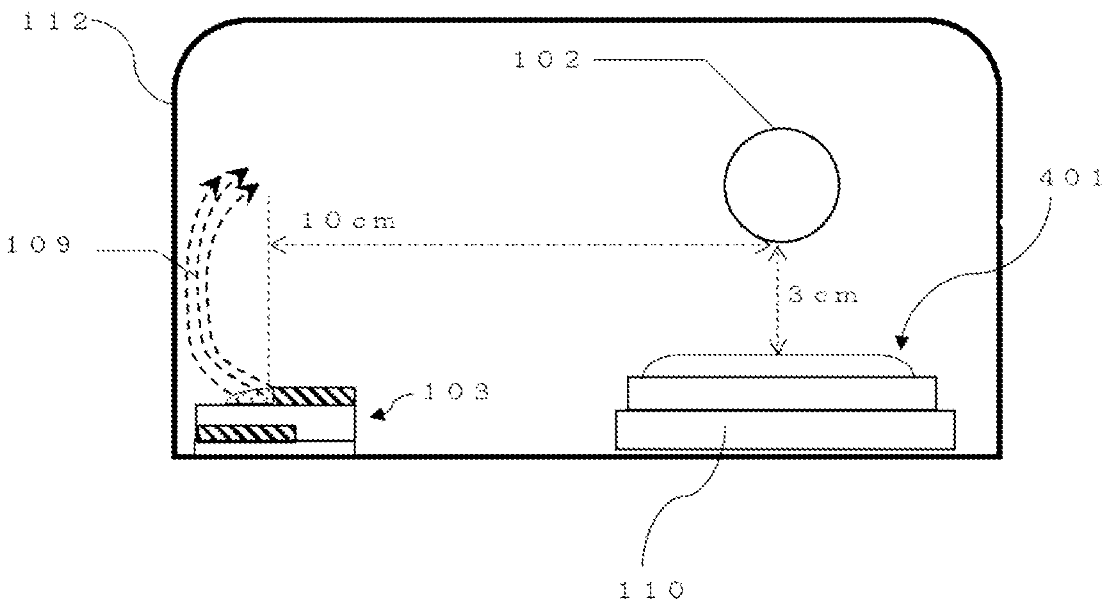
FIG. 5 is a schematic cross-sectional view of a sterilization device according to Comparative Example 4.

In the sterilization device of Example 1, the plasma actuator was arranged so that the induced flow flowed on the opposite side of the object to be treated as shown in FIG. 5, the distance between the edge of the first electrode and the center of the object to be treated was 10 cm, and the distance between the ultraviolet light source and the surface of the object to be treated was 3 cm.

Then, a voltage was applied to the plasma actuator under the same conditions as in Example 1, and the inside of the sterilization container was filled with ozone so that the ozone concentration in the surface region of the surface to be treated was 40 ppm. After that, the sample for evaluation was moved from the preliminary chamber into the sterilization chamber and placed on the mounting table so that the ozone concentration in the sterilization container did not decrease. Subsequently, in the same manner as in Example 1, the sample for evaluation was irradiated with ultraviolet light from the ultraviolet light source for 5 min for sterilization. Subsequent operations were carried out in the same manner as in Example 1, and the number of developed colonies was counted and evaluated.

TABLE 1

| | Set angle | | | Configuration of plasma actuator | | | Ozone concentration (ppm) | | Sterilization performance evaluation result |
|---|---|---|---|---|---|---|---|---|---|
| | PA incident angle (°) | UV incident angle (°) | UV peak wavelength (nm) | Thickness of dielectric (μm) | Dielectric material | UV illuminance (μW/cm$^2$) | Surface region of the surface to be treated | $L_{UV}$/2 | (number of colonies is shown in parentheses) |
| Example 1 | 0 | 90 | 254 | 150 | Glass | 487 | 40 | 8 | − (0) |
| Example 2 | 0 | 90 | 280 | 150 | Glass | 487 | 40 | 8 | − (0) |
| Example 3 | 0 | 90 | 254 | 200 | Glass | 487 | 35 | 7 | − (0) |
| Example 4 | 0 | 90 | 254 | 50 | Glass | 487 | 45 | 9 | − (0) |
| Example 5 | 0 | 90 | 254 | 150 | Polyimide | 487 | 37 | 7 | − (0) |
| Comparative Example 1 | 0 | 90 | — | 150 | Glass | 0 | 0 | 0 | + + + |
| Comparative Example 2 | 0 | 90 | 254 | 150 | Glass | 487 | 0 | 0 | ± (5) |
| Comparative Example 3 | 0 | 90 | — | 150 | Glass | 0 | 50 | 10 | + + (34) |
| Comparative Example 4 | — (Corner of device) | 90 | 254 | 150 | Glass | 487 | 40 | 40 | + (12) |

In the table, PA represents the plasma actuator, and UV represents ultraviolet rays.

Example 6

1. Production of Device for Treatment with Active Oxygen and Evaluation of Characteristics First, the housing 601 of the active oxygen supply device 600 shown in FIG. 7 was prepared. FIG. 6 is a plan view of the active oxygen supply device shown in FIG. 7 as viewed from the side of the housing 601 having the opening 605. The size of the housing was 20 mm in height, 150 mm in depth, and 20 mm in width when placed with the opening 605 facing vertically downward. The opening 605 had a width of 7 mm and a length of 15 mm. The opening 605 was provided so that the longitudinal direction thereof coincided with the depth direction of the housing, as shown in FIG. 6.

Further, the plasma actuator 103 was produced in the same manner as in Example 1. The plasma actuator 103 was then fixed to the inner wall of the housing 601 as shown in FIG. 7. Specifically, one end of the first electrode 203 of the plasma actuator 103 was at a position horizontally aligned with the center of the ultraviolet light source 102 and was fixed so that the induced flow 109 from the plasma actuator 103 flowed from the opening 605. Here, the distance (reference numeral 607 in FIG. 8) between the surface of the plasma actuator 103 facing the ultraviolet light source and the ultraviolet light source 102 was set to 2 mm, and the distance (reference numeral 609 in FIG. 8) between the lower end of the plasma actuator 103 and the lower end (outer side of the housing) of the opening 605 was set to 1 mm. As the ultraviolet light source 102, a cold-cathode ultraviolet lamp (trade name: UW/9F89/9, manufactured by Stanley Electric Co., Ltd., peak wavelength=254 nm) was used in the same manner as in Example 1.

For the active oxygen supply device 600 thus obtained, an illuminometer (trade name: Spectral Irradiance Meter USR- 45D, manufactured by Ushio Inc.) was placed on the surface of the glass plate 201 of the plasma actuator 103 facing the ultraviolet lamp and the illuminance of ultraviolet light was measured. From the integrated value of the spectrum, the illuminance was 1370 μW/cm$^2$. Also, the illuminance of ultraviolet light when the illuminometer was placed in contact with the opening 605 was 0.3 μW/cm$^2$. From this, it was confirmed that there was substantially no leakage of ultraviolet light from the opening.

Next, a voltage having a sine waveform with an amplitude of 2.4 kV and a frequency of 80 kHz was applied between both electrodes of the plasma actuator 103 without turning on the power of the ultraviolet lamp so as not to be affected by decomposition of ozone by ultraviolet light. After 5 minutes, 50 ml of the induced flow flowing out of the opening was sampled. The sampled gas was sucked into an ozone detection tube (trade name: 182SB, manufactured by Komyo Rikagaku Kogyo K.K.), and the concentration of ozone contained in the induced flow from the plasma actuator was measured to be 70 ppm (read value×2).

Next, a voltage having a sine waveform with an amplitude of 2.4 kV and a frequency of 80 kHz was applied between both electrodes of the plasma actuator, and the ultraviolet lamp was turned on so that the illuminance on the surface of the glass plate 201 of the plasma actuator 103 facing the ultraviolet lamp was 1370 μW/cm$^2$. Then, the ozone concentration in the induced flow flowing out from the opening at this time was measured in the same manner as described above. The result was 18 ppm. Based on these results, it is considered that this induced flow includes active oxygen generated by decomposing 52 ppm of ozone by ultraviolet light.

2-1. Treatment (Sterilization) Test (1) Preparation of Sample for Sterilization Test Three samples for evaluation produced for the verification test of sterilization performance in Example 1 were prepared.

As in Example 1, a stamp medium (trade name: PETAN CHECK 25 PT1025 manufactured by Eiken Chemical Co., Ltd.) was pressed for 10 sec under a pressure of 25 g/cm$^2$ against a door knob that had not been wiped with water, alcohol, etc. for a week in a location where an unspecified number of people entered and exited, and then the stamp medium was allowed to stand for 12 h in an environment at a temperature of 37° C. A colony grown in the stamp medium was collected using a sterile cotton swab and dispersed in distilled water to prepare a bacterial solution. A new stamp medium (PETAN CHECK 25 PT1025 manufactured by Eiken Chemical Co., Ltd.) was smeared with 0.1 ml of a diluted bacterial solution obtained by diluting this bacterial solution 10-fold with distilled water, and allowed to stand for 12 h in an environment at a temperature of 37° C. As a result, growth of bacteria of 200 CFU/ml to 300 CFU/ml was observed. Then, 0.1 ml of the diluted bacterial solution was smeared on the entire surface of a glass plate (15 mm long, 15 mm wide, 2 mm thick) that had been cleaned with alcohol having a concentration of 70%. After that, the glass plate was placed in an environment at a temperature of 37° C. for 1 h to remove moisture. Thus, a total of three samples for sterilization tests were prepared.

(2) Sterilization Test

The active oxygen supply device was placed on the surface to be treated of each sample so that the distance (reference numeral 611 in FIG. 8) between the surface (outer surface) of the housing having the opening and the surface to be treated was 2 mm. At this time, the center position in the width direction of the sample (left-right direction in FIG. 8) was aligned with the center position in the width direction of the opening and also aligned with the center position in the depth direction of the sample (the depth direction of the paper surface in FIG. 8) and the center position in the longitudinal direction of the opening. Next, a voltage having a sine waveform with an amplitude of 2.4 kV and a frequency of 80 kHz was applied to the plasma actuator, the ultraviolet lamp was turned on so that the illuminance on the surface of the glass plate 201 of the plasma actuator 103 facing the ultraviolet lamp was 1370 μW/cm$^2$, the induced flow was irradiated with ultraviolet light for 30 sec, the induced flow including active oxygen was caused to flow out from the opening, and active oxygen was supplied to the surface to be treated (treatment time: 30 sec).

Next, a stamp medium (trade name: PETAN CHECK 25 PT1025 manufactured by Eiken Chemical Co., Ltd.) was pressed for 10 sec under a pressure of 25 g/cm$^2$ against the surface to be treated of the sample, and then the stamp medium was allowed to stand for 12 h in an environment at a temperature of 37° C. The number of surviving bacteria was calculated from the number of colonies grown on the medium. The average value of the number of surviving bacteria obtained from each sample was multiplied by 10 and used as the number of colonies in the sterilization test according to the present example. Based on the number of colonies obtained, the sterilization performance was evaluated according to the following criteria (Ten Cate determination display method).

−: No growth
±: Number of colonies <10
+: Number of colonies 10 to 29
++: Number of colonies 30 to 100
+++: Number of colonies >100
++++: Countless colonies 2-2. Treatment (Bleaching) Test (1) Preparation of Samples for Bleaching Test Chili sauce (trade name: PEPPER SAUCE, manufactured by Tabasco Co.) was filtered through a long-fiber nonwoven fabric (trade name: BEMCOT M-3II, manufactured by Asahi Kasei Corporation) to remove solids. A paper wiper (trade name: KIMWIPE S-200, manufactured by Nippon Paper Crecia Co., Ltd.) was immersed in the obtained liquid for 10 min. Subsequently, the paper wiper was taken out and washed with water. Washing with water was repeated until the washing liquid was no longer visually colored. Thereafter, drying was performed. Then, three samples having a length of 15 mm and a width of 15 mm were cut out from the paper wiper dyed red with the chili sauce.

(2) Bleaching Test

The active oxygen supply device was placed on each sample so that the distance (reference numeral 611 in FIG. 8) between the surface having the opening of the housing (outer surface) and the surface to be treated was 2 mm. At this time, the center position in the width direction of the sample (left-right direction in FIG. 8) was aligned with the center position in the width direction of the opening and also aligned with the center position in the depth direction of the sample (the depth direction of the paper surface in FIG. 8) and the center position in the longitudinal direction of the opening. Next, a voltage having a sine waveform with an amplitude of 2.4 kV and a frequency of 80 kHz was applied to the plasma actuator, the ultraviolet lamp was turned on so that the illuminance on the surface of the glass plate 201 of the plasma actuator 103 facing the ultraviolet lamp was 1370 μW/cm$^2$, the induced flow was irradiated with ultraviolet light for 20 min, and the induced flow including active oxygen was supplied to a part of the surface to be treated (treatment time: 20 min). Next, the active oxygen supply device was removed from the surface to be treated, and the degree of decolorization was visually observed in comparison with the sample before the treatment and evaluated according to the following criteria.

A: Completely bleached.

B: The red color of the chili sauce remained slightly.

C: The red color of the chili sauce remained somewhat.

D: There was no difference in color from the portion where active oxygen was not supplied.

2-3. Treatment (Deodorization) Test (1) Preparation of Sample for Deodorization Test A paper wiper (KIMWIPE S-200, manufactured by Nippon Paper Crecia Co., Ltd.) was immersed in Fabric Mist (trade name: Fabric Mist-Linen, manufactured by SABON Co.) for 10 min, then taken out and allowed to dry naturally for 6 h. Then, three samples having a length of 15 mm and a width of 15 mm were cut out from the paper wiper.

C: A weak odor that can be recognized as the odor of Fabric Mist (cognitive threshold).

D: No difference from untreated sample.

Comparative Examples 5 to 7

The conditions for Comparative Examples 5 to 7 were the same as those for Example 6, except for the following features.

Comparative Example 5: No voltage was applied to the plasma actuator, and no ultraviolet irradiation was performed.

Comparative Example 6: Ultraviolet irradiation was performed for 2 min without applying voltage to the plasma actuator.

Comparative Example 7: A voltage was applied to the plasma actuator for 2 min, and no ultraviolet irradiation was performed.

TABLE 2

| | Set angle | | Plasma actuator configuration | | | Ozone concentration (ppm) | Sterilization performance evaluation result | | |
|---|---|---|---|---|---|---|---|---|---|
| | PA incident angle (°) | UV peak wavelength (nm) | Thickness of dielectric (μm) | Dielectric material | UV illuminance (μW/cm$^2$) | Surface region of the surface to be treated | (number of colonies is shown in parentheses) | Bleaching test evaluation result | Deodorization test evaluation result |
| Example 6 | 90 | 254 | 150 | Glass | 1370 | 40 | – (0) | A | A |
| Comparative Example 5 | 90 | — | 150 | Glass | 0 | 0 | + + + | D | D |
| Comparative Example 6 | 90 | 254 | 150 | Glass | 1370 | 0 | + + + | D | D |
| Comparative Example 7 | 90 | — | 150 | Glass | 0 | 50 | + + (34) | C | C |

(2) Deodorization Test

The active oxygen treatment device was placed on the surface to be treated of each sample so that the distance (reference numeral 611 in FIG. 8) between the surface having the opening of the housing (outer surface) and the surface to be treated was 2 mm. At this time, the center position in the width direction of the sample (left-right direction in FIG. 8) was aligned with the center position in the width direction of the opening and also aligned with the center position in the depth direction of the sample (the depth direction of the paper surface in FIG. 8) and the center position in the longitudinal direction of the opening. Next, a voltage having a sine waveform with an amplitude of 2.4 kV and a frequency of 80 kHz was applied to the plasma actuator, the ultraviolet lamp was turned on so that the illuminance on the surface of the glass plate 201 of the plasma actuator 103 facing the ultraviolet lamp was 1370 μW/cm$^2$, the induced flow was irradiated with ultraviolet light for 20 sec, and the induced flow including active oxygen was supplied to a part of the surface to be treated (treatment time: 20 sec). Next, the active oxygen supply device was removed from the surface to be treated, and the odor remaining in the treated sample was evaluated according to the following strength criteria in comparison with the sample before the treatment with active oxygen. The evaluation was performed by 5 subjects, and strength criteria selected by at least 3 subjects were adopted.

A: Odorless.

B: An odor that can barely be detected (detection threshold).

2-4. Treatment (Sterilization of *Escherichia Coli*) Test (1) Using the active oxygen supply device used in Example 6, an *Escherichia coli* sterilization test was carried out according to the following procedure. All instruments used in this sterilization test were sterilized with high-pressure steam using an autoclave. In addition, this sterilization test was conducted in a clean bench.

First, *Escherichia coli* (trade name "KWIK-STIK (*Escherichia coli* ATCC8739), manufactured by Microbiologics)" was placed in an Erlenmeyer flask containing LB medium (distilled water was added to 2 g of tryptone, 1 g of yeast extract, and 1 g of sodium chloride to make 200 ml) and cultured with shaking at 80 rpm at a temperature of 37° C. for 48 h. The bacterial suspension of *Escherichia coli* after culturing was 9.2×10$^9$ (CFU/ml).

Using a micropipette, 0.010 ml of the cultured bacterial suspension was dropped onto a slide glass (Matsunami glass, model number: S2441) having a length of 3 cm, a width of 1 cm, and a thickness of 1 mm, and the bacterial suspension was coated on the entire surface on one side of the slide glass with the tip of the micropipette to prepare sample No. 6-1. Samples Nos. 6-2 and 6-3 were produced in a similar manner.

Next, sample No. 6-1 was immersed for 1 h in a test tube containing 10 ml of buffer solution (trade name "Gibco PBS", Thermo Fisher Scientific Inc.). To prevent the bacterial suspension on the slide glass from drying, the time from dropping the bacterial suspension onto the slide glass to immersing it in the buffer solution was set to 60 sec.

Next, 1 ml of the buffer solution into which sample No. 6-1 was immersed (hereinafter referred to as "1/1 solution") was placed in a test tube containing 9 ml of buffer solution to prepare a diluted solution (hereinafter referred to as "1/10 diluted solution"). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution and smeared on a stamp medium (PETAN CHECK 25, PT1025, manufactured by Eiken Chemical Co., Ltd.). This operation was repeated to prepare two stamp media smeared with the 1/1 solution. The two stamp media were placed in a thermostat (trade name: IS600; manufactured by Yamato Scientific Co., Ltd.) and cultured at a temperature of 37° C. for 24 h. The number of colonies generated on the two stamped media was counted, and the average value was calculated.

For the 1/10 diluted solution, 1/100 diluted solution, 1/1000 diluted solution and 1/10,000 diluted solution, two smeared stamp media were prepared and cultured for each diluted solution in the same manner as above. Then, the number of colonies generated in each stamp medium for each diluted solution was counted, and the average value was calculated. Table 3 shows the results.

TABLE 3

| | Sample No. 6-1 (blank) |
|---|---|
| 1/1 solution | >300 |
| 1/10 diluted solution | >300 |
| 1/100 diluted solution | >300 |
| 1/1000 diluted solution | 179 |
| 1/10000 diluted solution | 21 |

From the results shown in Table 3 above, it was found that the number of colonies when culturing the 1/10,000 diluted solution was 21 and therefore, the number of bacteria present in 0.050 ml of the 1/1 solution related to sample No. 6-1 was $21 \times 10^4 = 210{,}000$ (CFU).

Next, the following operations were performed with respect to samples Nos. 6-2 and 6-3.

A recess having a length of 3.5 cm long, a width of 1.5 cm, and a depth of 2 mm was provided in the center of a plastic flat plate having a length of 30 cm, a width of 30 cm, and a thickness of 5 mm, and the slide glass was placed into the recess so that the surface of the slide glass of each sample on the side opposite that coated with the bacterial solution was in contact with the bottom surface of the recess. Then, the active oxygen supply device was placed on the upper surface of the plastic plate so that the center in the longitudinal direction of the opening of the active oxygen supply device coincided with the center in the longitudinal direction of the recess and also so that the center in the width direction of the opening of the active oxygen supply device coincided with the center in the lateral direction of the recess. Since the depth of the recess was 2 mm and the thickness of the slide glass was 1 mm, the surface of each sample to which the bacterial solution had adhered did not come into direct contact with the opening of the active oxygen supply device.

Next, the active oxygen supply device was actuated, and the surface of the slide glass coated with the bacterial solution was treated with an induced flow including active oxygen. The treatment time was 2 sec for sample No. 6-2 and 10 sec for sample No. 6-3. In addition, the time from dropping the bacterial solution onto the slide glass to immersing in the buffer solution was set to 60 sec so that the bacterial solution on the slide glass did not dry in the treatment process using the active oxygen supply device.

The treated samples Nos. 6-2 and 6-3 were immersed for 1 h in a test tube containing 10 ml of buffer solution (trade name "Gibco PBS", Thermo Fisher Scientific Inc.). Next, 1 ml of the buffer solution into which each sample was immersed (hereinafter referred to as "1/1 solution") was placed in a test tube containing 9 ml of buffer solution to prepare a diluted solution (1/10 diluted solution). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution of each sample and smeared on a stamp medium (PETAN CHECK 25, PT1025, manufactured by Eiken Chemical Co., Ltd.). This operation was repeated to prepare two stamp media smeared with the 1/1 solution for each sample. A total of four stamp media were placed in a thermostat (trade name: IS600; manufactured by Yamato Scientific Co., Ltd.) and cultured at a temperature of 37° C. for 24 h. The number of colonies generated on the two stamped media was counted, and the average value was calculated.

For the 1/10 diluted solution, 1/100 diluted solution, 1/1000 diluted solution and 1/10,000 diluted solution related to each sample, two smeared stamp media were prepared and cultured for each diluted solution in the same manner as above. Then, the number of colonies generated in each stamp medium for each diluted solution was counted, and the average value was calculated. Table 4 shows the results.

TABLE 4

| | Sample No. 6-2 (treatment time 2 sec) | Sample No. 6-3 (treatment time 10 sec) |
|---|---|---|
| 1/1 solution | >300 | 0 |
| 1/10 diluted solution | >300 | 0 |
| 1/100 diluted solution | 37 | 0 |
| 1/1000 diluted solution | 5 | 0 |
| 1/10000 diluted solution | 0 | 0 |

From the number of colonies in the 1/1000 diluted solution related to sample No. 6-2 after the treatment, it was found that the number of bacteria in 0.050 ml of the 1/1 solution related to sample No. 6-2 was $5 \times 10^3 = 5000$ (CFU). Therefore, in this example, the sterilization rate of *Escherichia coli* when the treatment time was 2 sec was 97.6% (=(210,000−5000)/210,000×100).

Also, from the number of colonies in the 1/1 solution related to sample No. 6-3 after the treatment, it was found that the number of bacteria in 0.050 ml of the 1/1 solution related to sample No. 6-3 was 0 (CFU). Therefore, in this example, the sterilization rate of *Escherichia coli* when the treatment time was 10 sec was 99.999% (=(210,000−1)/210,000×100) or higher.

(2) Samples Nos. C6-1 and C6-2 were prepared in the same manner as sample No. 6-1. These samples were treated in the same manner as in (1) above, except that the ultraviolet lamp of the active oxygen supply device was not turned on. Therefore, samples Nos. C6-1 and C6-2 were treated with ozone in the induced flow. The treatment time was 2 sec for sample No. C6-1 and 10 sec for sample No. C6-2. For samples Nos. C6-1 and C6-2, immersion and dilution in a buffer solution were performed in the same manner as for sample No. 6-1 in (1) above. Next, two smeared stamp media were prepared and cultured with respect to each of the 1/1 solution, 1/10 diluted solution, 1/100 diluted solution, 1/1000 diluted solution and 1/10,000 diluted solution related to each of sample No. C6-1 and sample No. C6-2 in the same manner as for sample No. 6-1 in (1) above. Then, the number of colonies generated in each stamp medium related to the 1/1 solution and each diluted solution for each sample was counted, and the average value was calculated. Table 5 shows the results.

TABLE 5

| | Sample No. C6-1 (treatment time 2 sec) | Sample No. C6-2 (treatment time 10 sec) |
|---|---|---|
| 1/1 solution | >300 | >300 |
| 1/10 diluted solution | >300 | >300 |
| 1/100 diluted solution | >300 | >300 |
| 1/1000 diluted solution | 182 | 99 |
| 1/10000 diluted solution | 19 | 8 |

From the results of culturing the 1/10,000 diluted solution of sample No. C6-1 after treatment, among the above results, it was found that the number of bacteria present in 0.050 ml of the 1/1 solution related to sample No. C6-1 after treatment was $19\times10^4$=190,000 (CFU). Therefore, in the test example using sample No. C6-1, the sterilization rate of *Escherichia coli* was 9.5% (=(210,000−190,000)/210,000×100).

From the results of culturing the 1/10,000 diluted solution of sample No. C6-2, it was found that the number of bacteria present in 0.050 ml of the 1/1 solution for sample No. C6-2 was $8\times10^4$=80,000 (CFU). Therefore, in the test example using sample No. C6-2, the sterilization rate of *Escherichia coli* was 61.9% (=(210,000−80,000)/210,000×100).

From the above results, it was confirmed that the treatment using active oxygen can more reliably eliminate *Escherichia coli* in a short time as compared with the treatment with ozone alone.

(3) The slide glass used in the preparation of sample No. 6-1, was changed to qualitative filter paper (product number: No. 5C, manufactured by Advantec Co., Ltd.) having a length of 3 cm and a width of 1 cm. In addition, the bacterial solution was only dropped onto one side of the filter paper. Other than these, samples Nos. 7-1 and 7-2 were prepared in the same manner as sample No. 6-1.

Next, the following operations were performed with respect to sample No. 7-1.

A recess having a length of 3.5 cm long, a width of 1.5 cm, and a depth of 2 mm was provided in the center of a plastic flat plate having a length of 30 cm, a width of 30 cm, and a thickness of 5 mm. A filter paper having a length of 3.5 cm and a width of 1.5 cm was laid in the recess. Sample No. 7-1 was arranged on the filter paper so that the bacterial solution dropping surface thereof faced the filter paper laid on the bottom of the recess. Then, the active oxygen supply device was placed on the upper surface of the plastic plate so that the center in the longitudinal direction of the opening of the active oxygen supply device coincided with the center in the longitudinal direction of the recess and also so that the center in the width direction of the opening of the active oxygen supply device coincided with the center in the lateral direction of the recess. Since the depth of the recess was 2 mm and the thickness of the filter paper was 1 mm or less, the surface of each sample to which the bacterial solution had adhered did not come into direct contact with the opening of the active oxygen supply device. Next, the active oxygen supply device was actuated, and the surface of the bacterial solution dropping surface of the filter paper was treated with an induced flow including active oxygen. The treatment time was 10 sec. In addition, the time from dropping the bacterial solution onto the filter paper to immersing in the buffer solution was set to 60 sec so that the filter paper onto which the bacterial solution had been dropped did not dry in the treatment process using the active oxygen supply device.

The treated sample No. 7-1 was immersed for 1 h in a test tube containing 10 ml of buffer solution (trade name "Gibco PBS", Thermo Fisher Scientific Inc.). Next, 1 ml of the buffer solution after the immersion (hereinafter referred to as "1/1 solution") was placed in a test tube containing 9 ml of buffer solution to prepare a diluted solution (1/10 diluted solution). A 1/100 diluted solution, a 1/1000 diluted solution, and a 1/10,000 diluted solution were prepared in the same manner, except that the dilution ratio with the buffer solution was changed.

Next, 0.050 ml was sampled from the 1/1 solution and smeared on a stamp medium (PETAN CHECK 25, PT1025, manufactured by Eiken Chemical Co., Ltd.). This operation was repeated to prepare two stamp media smeared with the 1/1 solution. A total of two stamp media were placed in a thermostat (trade name: IS600; manufactured by Yamato Scientific Co., Ltd.) and cultured at a temperature of 37° C. for 24 h. The number of colonies generated on each stamped medium related to the 1/1 solution of sample No. 7-1 was counted, and the average value was calculated.

For 1/10 diluted solution, 1/100 diluted solution, 1/1000 diluted solution and 1/10,000 diluted solution, two smeared stamp media were prepared and cultured for each diluted solution in the same manner as above. Then, the number of colonies generated in each stamp medium for each diluted solution was counted, and the average value was calculated.

Further, as control samples, a 1/1 solution and 1/10 to 1/10000 diluted solutions were prepared in the same manner as above with respect to the untreated sample No. 7-2 as well, stamped media were prepared and cultured in the same manner, and the average number of colonies was calculated. Table 6 shows the results.

TABLE 6

| | Sample No. 7-1 (treatment time 10 sec) | Sample No. 7-2 (untreated) |
|---|---|---|
| 1/1 solution | 0 | >300 |
| 1/10 diluted solution | 0 | >300 |
| 1/100 diluted solution | 0 | 54 |
| 1/1000 diluted solution | 0 | 5 |
| 1/10000 diluted solution | 0 | 0 |

From the results of culturing of the 1/1000 diluted solution of sample No. 7-2, it was found that the number of bacteria present in 0.050 ml of the 1/1 solution related to sample No. 7-2 was $5\times10^3$=5000 (CFU). Further, the number of bacteria in 0.050 ml of the 1/1 solution related to sample No. 7-1 after the treatment was 0 (CFU). From this, it was found that the sterilization rate of *Escherichia coli* in the test using sample No. 7-1 was 99.98% ((5000−1/5000)×100) or more.

Here, sample No. 7-1 was treated with active oxygen on the surface opposite to the bacterial solution dropping surface of the filter paper related to sample No. 7-1. From this, it was understood that the sterilization treatment by actively supplying active oxygen to the object to be treated according to the present disclosure can sterilize not only *Escherichia coli* present on the surface of the filter paper but also *Escherichia coli* present inside the filter paper. In this respect, the method according to the present disclosure is superior to sterilization treatment using only UV, which sterilizes only the surface irradiated with UV light.

The present disclosure is not limited to the above embodiments, and various modifications and changes are possible without departing from the spirit and scope of the present disclosure. Accordingly, the following claims are appended to disclose the scope of the present disclosure.

What is claimed is:

1. A sterilization device comprising a sterilization container, wherein the sterilization container comprises, inside thereof, a plasma generator, an ultraviolet light source, and a mounting table mounting an object to be sterilized, wherein the plasma generator is a plasma actuator comprising:

a dielectric, a first electrode provided on a first surface of the dielectric, and a second electrode provided on a second surface opposite to the first surface of the dielectric and arranged obliquely with a shift across the dielectric to the first electrode, wherein, when a voltage is applied between the first electrode and the second electrode, the plasma actuator generates an induced flow including ozone from an edge of the first electrode along an exposed portion of the first surface of the dielectric that is not covered by the first electrode, wherein the induced flow is supplied to a surface of the object to be sterilized, wherein the ultraviolet light source is arranged so as to be capable of irradiating the surface of the object to be sterilized, and irradiates the induced flow with ultraviolet light and generates active oxygen in the induced flow, and wherein the surface of the object to be sterilized is sterilized inside the sterilization container.

2. The sterilization device according to claim 1, wherein the ultraviolet light emitted from the ultraviolet light source has a peak wavelength that is within a range of 220 nm to 310 nm.

3. The sterilization device according to claim 1, wherein the ultraviolet light emitted from the ultraviolet light source has an illuminance of 100 $\mu W/cm^2$ or more at a position corresponding to the surface of the object to be treated.

4. The sterilization device according to claim 1, wherein the plasma actuator generates the induced flow whose ozone concentration is 20 ppm or more measured at a position corresponding to the surface of the object to be treated.

5. The sterilization device according to claim 1, wherein the plasma actuator is arranged so that the surface of the object to be sterilized is included on an extension line in a direction along the exposed portion of the first surface of the dielectric from the edge of the first electrode.

* * * * *